United States Patent [19]
Rojas et al.

[11] Patent Number: 5,899,168
[45] Date of Patent: May 4, 1999

[54] SYNTHETIC DIET FOR REARING THE HYMENOPTEROUS ECTOPARASITOID, *CATOLACCUS GRANDIS*

[75] Inventors: Maria G. Rojas; Juan A. Morales-Ramos; Edgar G. King, all of Weslaco, Tex.

[73] Assignee: The United States of America, as represented by the Secretary of Agriculture, Washington, D.C.

[21] Appl. No.: 08/863,261

[22] Filed: May 27, 1997

Related U.S. Application Data

[63] Continuation of application No. 08/404,779, Mar. 15, 1995, abandoned.

[51] Int. Cl.[6] .................................................. A01K 67/033
[52] U.S. Cl. .............................. 119/6.5; 119/6.6; 119/6.7; 119/270
[58] Field of Search ............................... 435/240.2, 240.3, 435/240.31; 119/6.5, 6.6, 6.7, 270

[56] References Cited

U.S. PATENT DOCUMENTS 4,418,647   12/1983   Hoffman ........................................ 119/1

OTHER PUBLICATIONS

King, Edgar G., "Augmentation of Parasites and Predators for Suppression of Arthropod Pest", *Pest Management: Biologically Based Technologies*, Proceedings of Beltsville Symposium IVIII, USDA–ARS, Beltsville, MD, American Chemical Society, Washington, D.C., R. D. Lumsden & J. L. Vaughn [eds].

King, Edgar G., et al., "Integration of Boll Weevll Biological Control by Inoculative/Augmentative Releases of the Parasite *Catolaccus Grandis* in Short Season Cotton", Abstract, Cotton Insect Research and Control Conference, 1993 Beltwide Cotton Conferences, pp. 910–914.

Thompson, S. N., "Defined Meridic and Holldic Diets and Aseptic Feeding Procedures for Artificially Rearing the Ectoparasitoid *Exeristes roborator* (Fabricius)", Abstract, Annals of the Entomological Society of America, Mar. 1975, vol. 68, No. 2, pp. 220–226.

Guerra, Antonio A., et al., "In Vitro Rearing of *Bracon Mellitor* and *Catolaccus grandis* with Artificial Diets Devoid of Insect Components", *Entomol. Exp. Appl.* 1993, 68, pp. 303–307.

Guerra, Antonio A., et al., "An in vitro Rearing System for the Propagation of the Ectoparasitoid *Catolaccus grandis*", *Entomol. Exp. Appl.*, 1994, 72, pp. 11–16.

*Primary Examiner*—Gollamudi S. Kishore
*Attorney, Agent, or Firm*—M. Howard Silverstein; Randall E. Deck; John D. Fado

[57] ABSTRACT

An improved artificial diet or growth medium for rearing the insect parasitoid *Catolaccus grandis* is disclosed. The growth medium is composed of amino acid, mineral, vitamin, lipid, and carbohydrate fractions which are present in amounts and proportions effective to support growth of *Catolaccus grandis,* and the amino acid fraction includes alanine, glutamic acid, histidine and proline at concentrations of about 3.0–5.0%, 8.4–9.4%, 10.0–15.1% and 11.7–12.8%, by weight, respectively. The growth medium is suitable for mass propagation of *C. grandis* from egg to adult for their subsequent release as biocontrol agents. Alternatively, the growth medium may be used to support growth of adult female wasps of *C. grandis* for use as breeding stock for continued mass propagation.

18 Claims, No Drawings

SYNTHETIC DIET FOR REARING THE HYMENOPTEROUS ECTOPARASITOID, *CATOLACCUS GRANDIS*

CROSS-REFERENCED TO RELATED APPLICATIONS

This application is a continuation of application Ser. No. 08/404,779, filed Mar. 15, 1995, now abandoned, the contents of which are incorporated herein.

BACKGROUND OF THE INVENTION

1. Field of Invention

This invention relates to an improved artificial diet for rearing *Catolaccus grandis*, an ectoparasite of the boll weevil.

2. Description of the Prior Art

In recent years, the potential of the ectoparasitoid *Catolaccus grandis* (Burks) as a biological control agent against the boll weevil, *Anthonomus grandis* Boheman, has been established by a number of investigators including Johnson et al. (1973, Environ. Entomol., 2.112–118), Morales-Ramos & King (1991, Evaluation of *Catolaccus grandis* (Burks) as a Biological Control Agent Against the Cotton Boll Weevil, page 724, In D. J. Herber & D. A. Richter [eds.], Proc. Beltwide Cotton Conferences 1991, Vol. 2, Proc. National Cotton Council of America, Memphis, Tenn.), Morales-Ramos & Cate (1992, Ann. Entomol. Soc. Am., 85:469–476), Summy et al. (1992, Southwest. Entomol., 17:279–288), and Morales-Ramos et al. (1994, Suppression of the Boll Weevil First Generation by Augmentative Releases of *Catolaccus grandis* in Aliceville, Ala., pp. 958–964, In D. J. Herber & D. A. Richter [eds.], Proc. Beltwide Cotton Conferences 1994, Vol. 2, National Cotton Council of America, Memphis, Tenn.). A number of biological attributes of *C. grandis* have been reported which enhance its utility as a biological control agent. These attributes include higher fecundity than that of the boll weevil (Morales-Ramos & Cate, ibid); adaptability to a variety of environments, including Mississippi (Johnson et al., ibid), Central Texas (Cate et al., 1990, Pests of Cotton, pp. 17–29, In D. H. Habeck, F. D. Bennett & J. H. Frank [eds.], Classical Biological Control in the Southern United States, South. Coop. Ser. Bull. 355), the Rio Grande Valley (Summy et al., ibid), and North Alabama (Morales-Ramos et al., 1994, ibid); high searching efficiency under low host population densities (Morales-Ramos & King, 1991, ibid); ability to search for hosts on the ground where the susceptible boll weevil stages occur (Summy et al., 1992, ibid); synchrony with the boll weevil life cycle (Morales-Ramos & Cate, 1993, Environ. Entomol., 22:226–233); and adaptability to ranges of temperatures similar to those tolerated by the boll weevil (Morales-Ramos & Cate 1992, Environ. Entomol., 21:620–627).

Augmentative releases of *C. grandis* have been successfully used to control boll weevil populations in experimental fields in the Rio Grande Valley as described by Summy et al. (1993, Suppression of Boll Weevil Infestations by Augmentative Releases of *Catolaccus grandis*, pp. 908–909, In D. J. Herber & D. A. Richter [eds.], Proc. Beltwide Cotton Conferences Vol. 2, National Cotton Council of America, Memphis, Tenn.) and in commercial cotton fields in Aliceville, Ala. as described by Morales-Ramos et al. (1994, ibid). However, because *C. grandis* lacks the ability to overwinter in the U.S. (Johnson et al., ibid), populations of this ectoparasitoid must be rereleased each year. The use of *C. grandis* as a biological control agent against the boll weevil therefore depends on the development of mass propagation technology.

The current method of mass propagation consists of encapsulating boll weevil larvae in Parafilm® (Cate, 1987, Southwest. Entomol., 12:211–215). This method of encapsulation has been modified by Morales-Ramos et al. (1992, Feasibility of Mass Rearing of *Catolaccus grandis*, a Parasitoid of the Boll Weevil, pp. 723–726, In D. J. Herber & D. A. Richter [eds.], Proc. Beltwide Cotton Conferences 1992, Vol. 2, National Cotton Council of America, Memphis, Tenn.) and mechanized by Roberson & Harsh (1993, Mechanized Production Processes to Encapsulate Boll Weevil Larvae (*Anthonomus grandis*) for Mass Production of *Catolaccus grandis* (Burks), pp. 922–923, In D. J. Herber & D. A. Richter [eds.], Proc. Beltwide Cotton Conferences, Vol. 2, National Cotton Council of America, Memphis, Tenn.), but, the high costs of using these methods make the price of augmentative releases of *C. grandis* 5–10 times higher than other methods of boll weevil control.

Despite the success of *C. grandis* augmentative releases in controlling boll weevil populations in experimental fields, commercial application of this technology is greatly limited by the high costs of mass propagating this parasitoid. Mass propagation has been identified as a critical constraint in commercializing augmentative releases of natural enemies (King & Morrison, 1984, Some Systems for Production of Eight Entomophagous Arthropods, pp. 206–222. In E. G. King & N. C. Leppla [eds.], Advances and Challenges in Insect Rearing, USDA-Agric. Research Serv., New Orleans, La., p. 306). Development of artificial diets for in vitro rearing of parasitoids is viewed as the scientific advance necessary for opening the path for the commercial application of biological control by augmentation of natural enemies (King, 1993, Augmentation of Parasites and Predators for Suppression of Arthropod Pests, pp. 90–100, In R. D. Lumsden & J. L. Vaughn [eds.], Pest Management: Biologically Based Technologies, Proceedings of Beltsville Symposium XVIII, USDA-ARS, Beltsville, Md., American Chemical Society, Washington, D.C.).

Artificial diets for in vitro rearing of hymenopteran ectoparasitoids have been described. Thompson (1975, Ann. Entomol. Soc. Am., 68:220–226) described an artificial diet for *Exteristes roborator* (Fabricius), while Guerra et al. (1993, Entomol. Exp. Appl., 68:303–307) described an artificial diet for both *Bracon mellitor* Say and *C. grandis*. Both diets were devoid of insect components and were composed of amino acid, mineral, vitamin, lipid and carbohydrate fractions. The main differences between these two diets are found in the ratios and amounts of the amino acids in the amino acid fraction. Moreover, Thompson used albumin as a supplement and Guerra et al. used fresh egg yolk.

Guerra et al. subsequently modified the artificial diet described in the 1993 publication, replacing the antimicrobial agent, and adding an antimycotic, and describing an improved technique for egg deposition (1994, Entomol. Exp. Appl., 72:11–16).

Both Thompson and Guerra et al. reported successful development of parasitoids feeding on their respective diets. However, an extensive evaluation of the biological characteristics of the in vitro- reared parasitoids was not presented; and none of the parasitoids were field released. The difficulty of producing large numbers of in vitro- reared parasitoids of sufficient quality has probably been the most important factor limiting the evaluation of their biological attributes. Production of uniformly high quality parasitoids is critical to success of the augmentative release approach. The release of poor quality parasitoids may considerably reduce the degree of success of augmentation practices.

SUMMARY OF THE INVENTION

We have now discovered an improved artificial diet or growth medium for rearing the insect parasitoid *Catolaccus grandis*. The growth medium is composed of amino acid, mineral, vitamin, lipid, and carbohydrate fractions which are present in amounts and proportions effective to support growth of *Catolaccus grandis*. The amino acid fraction, which comprises a mixture of at least 19 amino acids, includes alanine, glutamic acid, histidine and proline at concentrations of about 3.0–5.0%, 8.4–9.4%, 10.0–15.1% and 11.7–12.8%, by weight, respectively. The growth medium is suitable for mass propagation of *C. grandis* from egg to adult for their subsequent release as biocontrol agents. Alternatively, the growth medium may be used to support growth of adult female wasps of *C. grandis* for use as egg-laying stock for continued mass propagation. Use of this medium to rear *C. grandis* yields ectoparasitoids of unexpectedly superior quality than attainable using previously disclosed artificial diets.

In accordance with this discovery, it is an object of this invention to provide an improved artificial diet for rearing ectoparasitoids of *C. grandis*.

Another object of this invention is to provide an artificial diet for rearing *C. grandis* which yields high quality ectoparasites.

A further object of this invention is to provide an artificial diet for rearing *C. grandis* which is free of insect components.

Other objects and advantages of this invention will become readily apparent from the ensuing description.

DETAILED DESCRIPTION OF THE INVENTION

The artificial diet or growth medium of this invention is formulated for supporting the growth of larvae of *Catolaccus grandis* Burks from the time of hatching until pupation, and/or for supporting growth of the adult female wasp. The medium is free from insect components such as hemolymph, and is suitable for the production of ectoparasitoids of *C. grandis* on a commercial scale at a relatively low cost. Moreover, the ectoparasitoids are of sufficient quality to function effectively as biocontrol agents against the boll weevil following their release into the field.

The growth medium is composed of an amino acid fraction, a mineral fraction, a vitamin fraction, a lipid fraction, and a carbohydrate fraction essential for the growth of *C. grandis* larvae and/or adults. The medium preferably includes further optional components, such as an antimicrobial agent, antioxidant and/or protein source, as described in greater detail hereinbelow.

The composition of the amino acid fraction is critical for the production of high quality ectoparasitoids. This amino acid fraction is composed of a mixture of amino acids including but not limited to alanine, arginine, asparagine, cysteine, glutamic acid, glutamine, glycine, histidine, isoleucine, leucine, lysine, methionine, phenylalanine, proline, serine, threonine, tryptophan, tyrosine and valine. Aspartic acid may be optionally included. Although these amino acids have been previously identified as components in an artificial diet for a plurality of ectoparasitoids, including *C. grandis*, as described by both Guerra et al. (1993, Entomol. Exp. Appl., 68:303–307) and Thompson (1975, Ann. Entomol. Soc. Am., 68:220–226), we have unexpectedly discovered that when the concentration of alanine, glutamic acid, histidine and proline within the amino acid fraction are between about 3.0–5.0%, 8.4–9.4%, 10.0–15.1% and 11.7–12.8%, by weight, respectively, ectoparasitoids are produced which are significantly superior to those produced using previously available artificial diets. Specifically, *C. grandis* reared on this medium exhibit substantially increased pupal weight, fecundity (number of eggs produced per adult female), progeny females (number of female pupae produced per adult female), and net reproductive rate ($R_o$, defined hereinbelow) in comparison with those produced on the artificial diets of the prior art. The concentrations of the remaining amino acids are variable but should be effective to promote growth of *C. grandis*. The actual concentrations selected may be determined by the practitioner skilled in the art. Without being limited thereto, the preferred amino acids and their concentrations within this fraction are shown in Table 1.

The mineral and vitamin fractions are similar to those described in the diets of Guerra et al. (1993, ibid) and Thompson (1975, ibid), the contents of each of which are incorporated by reference herein, and vary only in the concentrations of the inorganic salts and vitamins therein. In summary, the mineral fraction comprises $CaCl_2$, $CoCl_2$, $FeCl_3$, $ZnCl_2$, $K_2HPO_4$, $Na_2HPO_4$, $MnSO_4$, $MgSO_4$ and $CuSO_4$. As indicated by Thompson, these inorganic salts may be prepared as three separate aqueous stock solutions to avoid precipitation.

The vitamin fraction comprises an aqueous mixture of biotin, Ca pantothenate (hemi Ca d-pantothenic acid), choline chloride, folic acid, myo-inositol, nicotinamide, pyridoxal HCl, riboflavin, and thiamine. Inclusion of vitamin $B_{12}$ (cyanocobalamin) is optional. The vitamin fraction may also be prepared as aqueous stock solutions in the manner disclosed by Thompson (1975, ibid), whereby the riboflavin is dissolved in water, followed by the remaining vitamins.

Lipids in the growth medium include but are not limited to cholesterol in combination with free fatty acids, including linoleic acid, linolenic acid, oleic acid, palmitic acid, palmitoleic acid and stearic acid. To ensure adequate distribution of the lipids within the medium, the lipids should be formulated with an emulsifier to form an emulsion. The emulsifier and the concentration thereof used in the medium should be non-toxic to the subject ectoparasitoid. Although it is envisioned that a variety of emulsifiers may be employed, dilute aqueous solutions of lauryl sulfate, added at a concentration of less than or equal to about 160 mg lauryl sulfate per 100 ml of growth medium, particularly at about 100 mg/100 ml, are preferred.

Techniques for preparation of the lipid fraction were described by Thompson (1975, ibid) and Guerra et al. (1993, ibid). However, we have modified the formulation of the lipid fraction to reduce the amounts of potentially toxic agents, i.e. solvents, emulsifiers and bases, present therein. In a first preferred embodiment, the lipid fraction may be prepared by homogenizing cholesterol and the fatty acids with a small amount of a suitable organic solvent, such as acetone, and adding sufficient emulsifier to form an emulsion. A Lewis base, such as KOH, may be added to raise the pH of the emulsion to about 7.0.

While the lipid fraction may be prepared from cholesterol and fatty acids in pure or substantially pure form (e.g. reagent grade), in the alternative these components may be provided in an impure naturally occurring source or plant oil. For example, in accordance with another preferred embodiment, olive oil may be used in place of pure fatty acids. Surprisingly, olive oil also functions as a preservative, obviating the need for incorporation of antimicrobials. Similarly, egg yolk (fresh or dried) may be used as a source for cholesterol, to reduce or replace the pure cholesterol incorporated into the diet. Egg yolk also provides the dual benefit of functioning as a supplemental protein source as well.

Glucose is the preferred carbohydrate source for use in the growth medium. However, it is envisioned that other carbohydrates may also be used, such as trehalose.

Other adjuvants or supplements may also be incorporated into the medium to enhance the growth of *C. grandis*, prevent the growth of microbial contaminants, or prevent decomposition of the above-mentioned fractions. Addition of a supplemental protein source to the medium is particularly preferred for enhancing growth of larvae of *C. grandis.* While a plurality of protein sources are contemplated as being suitable for use herein, including hydrolyzed proteins such as yeast extract or peptone, use of egg yolk (fresh or dried) is preferred. As noted hereinabove, egg yolk not only provides a supplemental protein source, but may also supplement or supplant the cholesterol in the lipid fraction. When the medium is being used to support growth of adult wasps rather than larvae, egg yolk may be omitted from the medium.

A variety of antimicrobials and preservatives may be incorporated into the growth medium to prevent contamination thereof by bacteria and fungi. Suitable antimicrobials include broad spectrum antimycotics or antibacterial agents as are known in the art, such as gentamicin, or preferably Antimycotic and phosphoric acid. Antioxidants may also be incorporated into the growth medium for enhanced stability and shelf-life. Without being limited thereto, propionic acid is preferred. As mentioned hereinabove, olive oil may also be used in place of the antimicrobials.

Agar, carrageenan or other solidifying agents as are conventional in the art may be optionally incorporated into the growth medium when a solid or semi-solid formulation is desired. The choice between a solid or liquid formulation of the growth medium will of course be dependent upon the manner of presentation to the ectoparasitoid as described hereinbelow.

The concentration and amount of all of the components added to the medium should be effective to support growth of *C. grandis.* The absolute amount of the amino acid fraction provided in the diet, that is the combined amount of all amino acids in the amino acid fraction, should be between approximately 5.8 to 6.5 g per 100 ml of growth medium (exclusive of the volume of egg yolk and agar added, if any). The concentrations and amounts of the remaining components, including minerals, vitamins, lipids, carbohydrates, proteins, and other adjuvants are somewhat more variable, and may be determined by the practitioner skilled in the art. Without being limited thereto, preferred concentrations and amounts of these components are shown in Table 1. Amounts of the amino acid, mineral, vitamin, lipid, carbohydrate, antimicrobial and antioxidant fractions listed in Table 1 are presented as mg per 100 ml of growth medium exclusive of the volume of protein (egg yolk) or agar.

Techniques for rearing larvae of *C. grandis* in vitro on artificial diets were described previously by Guerra et al. (1993, ibid; and 1994, Entomol. Exp. Appl., 72:11–16), the contents of each of which are incorporated by reference herein, and may be used with the growth medium of this invention. Hoffman (U.S. Pat. No. 4,418,647), the contents of which is also incorporated by reference herein, described artificial host eggs for rearing ectoparasitoids which are suitable for use herein. In accordance with the preferred embodiment, solid or liquid growth medium is deposited in a suitable container such as a petri dish or multiwell plate and covered with a permeable membrane. When using liquid medium, an absorbent or other solid material, such as a gel, cotton, or particularly polyester pad, may be placed within the container to retain the medium. Moreover, because of the mobility of first and second instar larvae and their predisposition for cannibalism, multiwell plates or other compartmentalized containers are preferred for use with solid media to segregate developing larvae. Cannibalism has not been observed using liquid medium which has been dispensed onto polyester pads due to reduced mobility of the larvae thereon.

The permeable membrane covers may be formed from a variety of polymeric materials, including but not limited to paraffin, calcium alginate, polyethylene, polypropylene and Parafilm. Use of Parafilm as a cover for the plates is particularly advantageous as this membrane functions as an additional ovipositional stimulant for egg-laying adult females of *C. grandis.* Although the treatment of the membrane with other ovipositional stimulants such as hexane or other low molecular weight alkanes, has been reported by Guerra et al. (1994, ibid) to further enhance oviposition by the adult females, use of these compounds is not preferred due to potential toxicity to the female wasps, particularly if large amounts are used. The growth medium per se of this invention functions as an ovipositional stimulant for *C. grandis* females, but oviposition may be further enhanced by use of these additional stimulants. The membrane may also be molded with round dome-shaped or convex projections as described by Hoffman (U.S. Pat. No. 4,418,647) to even further stimulate oviposition. The covered plates containing growth medium are then exposed to gravid adult *C. grandis* females for a sufficient period of time to allow the ectoparasitoids to oviposit eggs directly through the membrane cover, generally about 4 to 8 hours. Any eggs adhering to the inner surface of the membrane may be readily removed by spraying the outer surface of the membrane with water and gently tapping the plates until the eggs drop onto the medium, as described by Guerra et al. (1994, ibid). The plates containing parasitoid eggs are then incubated at approximately 27° C. to allow the eggs to hatch, and the larvae to feed upon the diets and pupate therein. Emerging adult wasps are then collected for subsequent use.

By relying upon direct oviposition onto the medium by the female wasps, the above-mentioned technique allows mass rearing of *C. grandis* with a minimum of handling by laboratory personnel. In an alternative, albeit more labor intensive embodiment, eggs are first collected using boll weevil larvae which have been encapsulated in a Parafilm sheet, such as described by Cate (1987, ibid) the contents of which are incorporated by reference herein. Females of *C. grandis* are exposed to the encapsulated boll weevil larvae for a sufficient period of time to allow oviposition. The parafilm sheet may then be removed and eggs adhering to its surface and/or to the larvae are manually collected such as by brushing. Following transfer onto the growth medium the eggs are incubated until emergence of adults as described hereinabove.

Although the newly emergent *C. grandis* wasps may be released directly into a target field infested with boll weevils, the effectiveness of these artificially reared wasps as biocontrol agents may be reduced. To achieve maximal efficacy, prior to their field release the emerging adult *C. grandis* are collected and exposed to boll weevils within environmental chambers in the production facility for a sufficient period of time to "train" the wasps and stimulate egg production by the females. Following this exposure, generally about 2 to 4 days, the wasps may be field released and exhibit substantially greater efficacy as biocontrol agents than wasps which have not been trained in this manner.

Formulations of this growth medium may also be effective as a diet for supporting growth of adults of *C. grandis,* and particularly egg-laying female wasps used as breeding stock for the mass propagation of this ectoparasitoid. The same formulation as shown in Table 1 may be used, although egg yolk and agar are preferably omitted. In accordance with this embodiment, adult wasps will feed upon the growth medium when exposed thereto. Oviposition may then be accomplished as described, generally when the female wasps are about 8 to 12 days old. In a preferred embodiment, we have discovered that if the adult females are exposed to boll weevil larvae for a short period of time prior to oviposition, egg production is substantially increased. During this exposure, the wasps do not need to feed on, but only touch or contact the boll weevil larvae to stimulate maximum egg production.

The following examples are intended only to further illustrate the invention and are not intended to limit the scope of the invention which is defined by the claims.

EXAMPLE 1

Artificial Diets

Four growth media of this invention, designated α-1, α-2, β and γ, were prepared and evaluated in comparison with the diets disclosed by Thompson (1975, ibid) and Guerra et al. (1993, ibid).

The composition of the amino acid, vitamin, lipid, and mineral fractions of the α-1, α-2, β and γ media are shown in Tables 2–5, respectively, while the remaining components are shown in Table 6.

The α-1, α-2, β and γ media were prepared as follows:

Amino acid mixture: Dissolve 6 g (6.3 g in α-2 media) of the amino acid mixtures of Table 2 in 70 ml (α-1, β and γ media) or 74 ml (α-1 media) milli-Q water in a 250 ml screw cap bottle. Add a 5-cm long teflon coated stirring bar. Place bottle in a 900-watts microwave oven and set temperature to high for 1.5 min. Manually shake the bottle for 10 sec. and place back in microwave oven for 30 sec. more. Place bottle on a magnetic plate and stir at medium speed until mixture cools to 30° C.

Vitamin fraction: The vitamins shown in Table 3 were dissolved in either 5 ml (for the a media) or 4 ml (for the β and γ media) of water.

Lipid mixture: weigh 50 mg of cholesterol and place it into a 25 ml glass homogenizer, add 0.5 ml of acetone, mix, and dry with a $N_2$ stream until it has a consistency of paste. Pipette 3 ml of the fatty acid mixture of Table 4 in acetone into the homogenizer. Dry mixture as above until it attains a pasty consistency, evaporating the acetone solvent. Add 5 ml of 2% lauryl sulfate solution (100 mg lauryl sulfate) and homogenize until the mixture is uniform.

Mineral fraction: Three stock solutions designated A, B and C, were prepared by dissolving salts shown in Table 5 in 2.5 ml (for the a media) or 2.0 ml (for the β and γ media) water (volumes are per stock solution).

Final diet mixture: Pipette the lipids into the amino acids. Rinse the homogenizer and plunger with 7 ml of 2M-KOH for a-diets and 4 ml of 3M-KOH for β and γ-diets. Autoclave mixture for 20 min. at 121° C. and then allow mixture to cool to room temperature. Under aseptic conditions, add 2.5 (for a-diets) and 2 ml (for β and γ diets) of each of the salt solutions sequentially (A, B, and C). Add 5 ml of 50 % aqueous glucose solution, and 5 ml (for α-diets) or 4 ml (for β and γ-diets) of vitamin solution, 1.5 ml of antibiotic (Antimycotic, Sigma A 7292), and 150 μl propionic acid (41.8 ml in 8.2 ml milli-Q water) and phosphoric acid (4.2 ml in 45.8 ml water) solutions.

All diets included egg yolk as a supplement. Portions of each basic diet from above (80 ml of the α and β diets and 86.65 g of the γ diet) were transferred by filtration (sterile polyester organza fabric) to a 150-ml sterile serum bottle. Twenty ml of fresh egg yolk was added with a sterile syringe to the a and β-diets, and 13.35 g dried egg yolk was added to the γ-diet (Sigma E-0625). Bottles were sealed with a sleeve type rubber stopper, labeled, and stored at 2° C. for up to 2 weeks. The unused portion of the diets, without egg yolk, could be stored at (−20° C.) for 30 days.

The α and β diets were used in liquid form, while the γ diet was a solid. A portion of the γ diet (89.22 g) was transferred with a sterile syringe transfer to a 50-ml sterile glass beaker. The beaker was placed in a water bath at 30° C. for 1 min and 10.78 g of sterile, 7% ultra pure agar (USB product number 10907) solution (kept in a water bath at 80° C.) was added.

The Thompson diet was prepared as described in the 1975 publication, and the Guerra et al. diet was prepared as described in the 1993 publication except that it was modified to assure successful development of the immature parasitoids. Lauryl sulfate at 200 mg/100 ml $H_2O$ was toxic to the parasitoid immatures; so, it was reduced to 100 mg/100 ml $H_2O$. The concentration of the KOH solution was changed from 1N to 2M (7 ml) to avoid dilution. Gentamicin was replaced by Antimycotic and a propionic acid-phosphoric acid solution to provide improved fungus control.

EXAMPLE 2

The α-1, α-2, β and γ growth media of Example 1 were compared with the diets of Guerra et al. and Thompson to evaluate the quality of *C. grandis* reared thereon.

Parasitoids used in this study were reared on boll weevil larvae as first described by Cate (1987, ibid). The boll weevil larvae were produced at the R. T. Gast Insect Rearing Laboratory, Mississippi State, Miss. Adult wasps were kept in plexiglass cages and were exposed to the encapsulated weevils inside these cages and developed at constant temperature. The time of exposure of host to the wasps and the environmental conditions of the rearing room were between 25–28° C. and 50–70% RH.

Diet presentation

Three ml of the liquid α, β and Thompson diets were placed in sterile petri dishes lined with sterile polyester padding (Pellon, 910 sew-in interfacing) and tightly covered with Parafilm to provide a barrier to stimulate the female parasitoids to oviposit. The γ diet was distributed (220 μl per well) in plastic disposable 128-well bioassay trays (Bio-Ba-128, C-D International, Pitman, N.J.) while still molten and the agar allowed to solidify for 1 min.

The Guerra et al. diet was presented in 24-well tissue culture dishes as described by the authors (Guerra et al. 1994, ibid). Although Guerra et al. reported that n-pentane, n-hexane, n-heptane, and isooctane acted as oviposition stimulants, none of these alkanes was used to stimulate oviposition in this study due to toxicity to the female wasps.

Egg Deposition Two methods were used to place the parasitoid eggs in the artificial diet. The first method was direct oviposition by the wasps onto the media. This was accomplished by covering the petri dishes (containing the artificial diets) with Parafilm as explained above. The Parafilm covering was molded with a round dome shaped projections to stimulate the female parasitoids. The Parafilm covered petri dishes were then exposed for 4 to 6 h to 5 to 10-d old parasitoid females, which had prior oviposition experience on boll weevil larvae. The petri dishes, containing the parasitoid eggs, were placed in an environmental chamber at 27° C. for 24 h to allow the eggs to hatch. Then, the Parafilm was removed and the petri dishes were covered with their lids and the edges were sealed with Parafilm to prevent intrusion by microbial contaminants. The parasitoids were allowed to develop inside the petri dishes at 27° C., and each larva was fed daily with 20 µl of the corresponding liquid diet (9 days).

This method did not require handling of the parasitoid eggs. However, this method was substantially more effective with the liquid diets ($\alpha$-1, $\alpha$-2, & $\beta$) than the solid diets ($\gamma$ and Guerra et al.). High rates of cannibalism by the parasitoid first instars occurred when the solid diet was utilized.

After ovipositing on the artificial diet, the parasitoid females were allowed to feed every other day on 25 encapsulated boll weevil larvae. Host feeding and direct contact with host larvae were essential to maintain a high level of egg production in *C. grandis* females.

The second method consisted of manually collecting the *C. grandis* eggs from cells containing encapsulated weevil larvae. A sheet of 25 encapsulated boll weevil larvae were exposed to the parasitoid females for 14 h. The Parafilm sheet covering the larvae was manually removed and the eggs stuck to its surface were brushed off with a fine painting brush (No. 0) on a wax paper sheet. The eggs were washed in a 0.1% bleach solution for 20 min and then rinsed with sterile distilled water in a polyester fabric filter (sterilized in autoclave). The eggs were manually transferred to the above mentioned media with the aid of a fine brush (10/0 Robert Simmons CP51). One egg was placed in each well; then all wells were closed with the provided plastic lids.

Evaluation of Parasitoid Fitness

Parasitoids developing on the test diets, as well as those developing on the natural host (boll weevils) as controls were held at 27±1° C. in a Percival environmental chamber. The development of 200 eggs was evaluated through the third instar in each diet and control to evaluate survival from cannibalism. One hundred parasitoid third instars developing in each diet and control were observed to the adult stage to evaluate survival.

Pupal Weight. Female parasitoid pupae reared in the different artificial diets (and controls) were collected 2 to 3 d after pupation and weighed in groups of varied numbers on a Mettler PM100 balance. The weights of the different groups were analyzed in a regression model using the GLM procedure of SAS software (SAS Institute 1988).

Fecundity and Sex Ratio. Seventy-two females emerging from each artificial diet and controls were individually reared in plastic petri dishes at constant 27±1° C. The sample size was chosen to estimate the population mean ($\mu$) of eggs/female and eggs/female/day within a confidence interval (E) of 20 and 1.5, respectively, with $\alpha$=0.05 using the equation:

$$n = ((Z_{\alpha/2})^2 \sigma^2)/E^2$$

where n is the sample size, $Z_{a/2}$=1.96 (from tables), o is the population standard deviation (estimated from sample 's'), and E is the confidence interval (Ott, 1984, An introduction to statistical methods and data analysis, second edition. Duxbury press, Boston, Mass., 775 pp).

Each female was provided with a single male, water and honey. Three days after emergence, each female parasitoid was exposed to 12 encapsulated boll weevil larvae each 24 h for 15 d. Dead females were not replaced, but, dead males were replaced during the first 13 d. Each day, the Parafilm capsules enclosing the parasitized weevils were opened to count the number of eggs oviposited per female. Then, they were resealed and returned to the environmental chamber for parasitoid development. Nine days later, the Parafilm capsules were reopened to count and sex the parasitoid pupae. The number of eggs oviposited by each female per day and the number and sex of developing progeny were recorded for the 15-d period.

The total number of eggs oviposited by each female during a 15-d period and the mean of eggs oviposited per day were used to compare the fecundity of females developing in the different diets against the controls. The sex for each of the female's progeny was recorded and a sex ratio established for the total progeny. The GLM procedure of the SAS software was used to analyze the data of fecundity and sex ratio.

Life tables were calculated for each group (developing in each of the artificial diets and controls) of 72 females for the 18 day experimental period (3 d of preoviposition and 15 d of oviposition). The '$m_x$' (female progeny produced per female) was estimated by multiplying the mean number of eggs produced per female of age 'x' by the mean proportion of developing females (=1−(1/sex ratio)) at age 'x'. The '$1_x$' (proportion surviving from birth to age 'x') at age 18 was compared between the different treatments and the controls. The net reproductive rate (R0) was calculated as:

$$R_o = \sum_{x=0}^{n} l_x m_x$$

where n is the oldest age (18 in this study) (Krebs, Ecology: The Experimental Analysis of Distribution and Abundance, 3rd ed., Harper & Row, New York, 1985).

Results and Discussion

The Thompson diet presented in liquid form did not yield adult *C. grandis*. From a total of 200 eggs planted in the Thompson diet, no second instars were recorded; all *C. grandis* larvae died during the first stadium.

Adults of *C. grandis* were successfully obtained from all other diets studied. Survival of *C. grandis* larvae from first to third instar was greatly affected by cannibalism. Differences were observed in the incidence of cannibalism between the different diets. The use of the polyester padding prevented cannibalism by reducing the ability of first and second instars to move. Therefore, one petri dish of liquid diet ($\alpha$ or $\beta$) lined with polyester padding yielded between 15–25 adult parasitoids. The mode of presentation of the Guerra et al. diet reduced cannibalism by isolating groups of larvae within wells. The yield of adult parasitoids in the modified Guerra et al. diet was between 10 to 14 per 24-well dish. Cannibalism was prevented in the $\gamma$-diet by isolating the parasitoid larvae in individual wells in the plastic disposable bioassay plates used.

Once the parasitoids molted to the third instar, cannibalism ceased. The mean survival of *C. grandis* from third instar to adult was 95±5% in the $\alpha$, $\beta$, $\gamma$, and Guerra et al. diets.

Pupal Weight. The weight of female parasitoid pupae reared in diets α-1, α-2, γ, and γ was significantly smaller than that of the controls (F=51.15, df 1, 62, P=0.0001) reared on boll weevils (Table 7). However, the pupal weight of females reared on these diets was significantly higher than the pupal weight of parasitoid females reared in the Guerra et al. diet (F=57.7, df 1, 62, P=0.0001)

Fecundity. The differences in fecundity observed between C. grandis females reared in the different diets and the controls had the same pattern as the pupal weight (Table 8). Females reared in diets α-1, α-2, β, and γ produced a significantly lower number of eggs compared to females reared in vivo (F=79.0, df 1, 292, P=0.0001). Similarly, the daily oviposition rate of females reared in these four diets were lower than those of females reared in boll weevil larvae (F=79.0, df 1, 292, P=0.0001). However, females reared in these four diets (α-1, α-2, β, and γ) showed a higher fecundity and daily oviposition rate than those reared in the Guerra et al. diet (F=139.3, df 1, 292, P=0.0001).

Progeny Sex Ratio. No significant differences were observed in the number of developing female progeny nor in progeny sex ratio (in females per male) between females reared in diets α-1, α-2, β, and γ (Table 9). Females reared in the α-2 diet did not show significant differences in either progeny sex ratio or surviving female progeny when compared to females reared in vivo. However, significantly lower number of females developed in the progeny of females reared in diets α-1, β, and γ than in females reared in vivo. The progeny sex ratio of females reared in diets α-2 and γ was not significantly different than that of females reared in vivo, but the progeny sex ratio of females reared in the β diet was significantly lower than that of the controls (F=4.73, df 1, 287, P=0.0305). Females reared in the Guerra et al. diet produced significantly less adult females in progeny than females reared in vivo (F=44.28, df 1, 287, P=0.0001) and in diets α-1, α-2, β, and γ (F=30.91, df 1, 287, P=0.0001). The progeny sex ratio of females reared in the Guerra et al. diet was significantly lower than t hat of females reared in vivo (F=13.94, df 1, 287, P=0.0002), in the α-1 diet (F=4.58, df 1, 287, P=0.033), in the α-2 diet (F=10.94, df 1, 287, P=0.0011), and in the γ diet (F=5.46, df 1, 287, P=0.0202). There was no significant difference in progeny sex ratio between females reared in Guerra et al. diet and those reared in the β diet.

Because females reared in all the treatments were provided with only 12 boll weevil larvae every day, the occurrence of superparasitism due to host limitation was common. Therefore, the mortality of C. grandis immature observed in this study was due mainly to cannibalism between first instars. This is probably the reason for the lack of significance of difference between controls and diets α-1, α-2, β, and γ in number of female progeny.

Net Reproductive Rate. The life table analysis showed a net reproductive rate ($R_o$) of 138.29 for females reared in vivo (Table 10). The highest $R_o$ value obtained from females reared in vitro was 116.4 from the γ diet. Diets α-1, α-2, and β had a $R_o$ value of 77.9, 85.1, and 93.7 respectively. The lowest $R_o$ value was 29.9 obtained from the Guerra et al. diet.

The α diets produced females with slightly higher fecundity than the β diet; however, females reared in the β diet had a higher survival rate ($1_x$) than those reared in the α diets (Table 10). Females reared in the Guerra et al. diet had survival rates comparable to those of females reared in vivo; however, their fecundity was considerably lower (about 75 %).

EXAMPLE 3

C. grandis reared on the γ growth medium described in Examples 1 and 2 were evaluated for efficacy against boll weevils under field conditions.

Materials and Methods

A ½ hectare cotton plot located at Rio Farms Inc. in Monte Alto, Tex. was chosen as the experimental field to test the in vitro reared C. grandis. This field was planted to Stoneville 132 cotton. No insecticides or other chemicals were used in this field, and mechanical cultivation was restricted to the first 30 days after planting. A control field was not necessary at this stage because no comparisons of fruit damage and cotton yield were planned, only boll weevil mortality was studied.

Parasitoid Rearing and Releases

Ten semiweekly releases of 400 C. grandis females were done during this experiment. The parasitoids were reared in the γ diet as described in Examples 1 and 2 except that the parasitoid eggs were initially obtained by using the Gamma diet as an oviposition stimulant rather than encapsulated boll weevil larvae. Approximately 5 ml of the diet were deposited in a plastic disposable petri dish, which was covered with Parafilm and then exposed to a colony of 100 females of C. grandis over a 4 h period. The parasitoid eggs were collected from the inner wall of the Parafilm cover. Once placed in the multiwell containers, the parasitoid eggs were allowed to develop to the pupal stage at constant 27° C. The parasitoid pupae were then collected and placed inside an emergence cage until they completed development.

The parasitoid females were held in the laboratory for 5 to 7 days after emergence before release in the experimental plot. During this time the parasitoid females were exposed to encapsulated boll weevils for 2 to 4 days to stimulate egg production (training).

When ready, the parasitoid females were collected by aspiration into in 11 paper canisters filled with shredded paper. Two canisters each containing 200 females each were prepared twice a week (Tuesdays and Fridays). The canisters were taken to the field the same day and opened in two previously marked release points. The selected release points were both in the central cotton row 40 m from the edge of the field and 70 m apart from each other.

Field Samples

Fifteen 1 $m^2$ random samples were taken weekly from the experimental plot. The samples consisted of all abscised fruiting material found within 1 $m^2$ sample points and all fruit present on one plant chosen randomly within each 1 $m^2$ sample point. All of the fruiting structures collected were then dissected in the laboratory under a microscope. All immature stages of boll weevil and C. grandis present were recorded in each sample. Densities of the different immature stages of the boll weevil were estimated from the random samples. Apparent percent parasitism of boll weevil second and third instars and pupae were calculated as the quotient of parasitized weevils and the sum of healthy and parasitized weevils. The percentage of unexplained mortality was calculated as the quotient of dead weevils (by unexplained reasons) and total weevils (dead, live, and parasitized) multiplied by 100. The percentage of mortality induced by parasitism was calculated as the quotient of parasitized boll weevils and total weevils multiplied by 100.

Results

The observed densities of the different stages of live immature boll weevils (in insects per $m^2$) are presented in Table 11. The C. grandis females reared in vitro inflicted a significant percentage of parasitism to second (36.4–100%) and third (18.4–57.1%) instars and pupae (0–75%) boll weevils (Table 12). This parasitism translated into a substantial mortality of these three boll weevil stages (63.2–100%, 31.9–60%, and 0–75% in seconds, thirds, and pupae respectively) (Table 13).

It is understood that the foregoing detailed description is given merely by way of illustration and that modifications and variations may be made therein without departing from the spirit and scope of the invention.

TABLE 1

Range of ingredient proportions for meridic diet preparation (mg/100 ml)

| Amino acids Percentages in Amino acid mix | Min–Max | Vitamins | Min–Max |
|---|---|---|---|
| Alanine | 3.1–4.83% | Biotin | 0.036–0.06 |
| Arginine | 1.77–3.0% | Ca pantothenate | 1.2–2.0 |
| Asparginine | 4.0–6.0% | Choline chloride | 120.0–200.0 |
| Aspartic acid | 0.0–0.33% | Folic acid | 0.06–0.1 |
| Cysteine | 1.83–4.77% | myo-Inositol | 9.0–15.0 |
| Glutamic acid | 8.5–9.33% | Nicotinamide | 3.0–5.0 |
| Glutamine | 0.78–5.17% | Pyridoxal HCl | 0.18–0.3 |
| Glycine | 2.9–3.0% | Riboflavin | 0.6–1.0 |
| Histidine | 10.05–15.0% | Thiamine | 0.12–2.0 |
| Isoleucine | 1.83–2.35% | Vitamin $B_{12}$ | 0.0–0.02 |
| Leucine | 1.83–2.57% | Lipids | |
| Lysine | 3.63–6.0% | Cholesterol | 0.0–70.0 |
| Methionine | 1.22–1.67% | Linolenic acid | 18.53–30.88 |
| Phenylalanine | 3.0–3.42% | Linolenic acid | 17.63–29.38 |
| Proline | 11.83–12.68% | Oleic acid | 41.78–69.63 |
| Serine | 3.18–5.17% | Palmitic acid | 46.5–77.5 |
| Threonine | 3.67–7.07% | Palmitoleic acid | 9.15–15.25 |
| Tryptophan | 6.0–6.1% | Stearic acid | 9.38–15.63 |
| Tyrosine | 6.0–16.53% | Lauryl sulfate | 80.0–160.0 |
| Valine | 4.43–5.17% | Carbohydrates | |
| Amino acid mix | 5800.0–6500.0 | Glucose | 240.0–280.0 |
| Minerals | | Antimicrobials | |
| Stock A | | Antimycotic | 0.0–1.05 |
| $CaCl_2$ | 18.0–30.0 | Phosphoric acid | 0.0–1.02 |
| $CoCl_2.6H_2O$ | 3.0–5.0 | Antioxidant | |
| $FeCl_3.6H_2O$ | 12.0–20.0 | Propionic acid | 0.0–62.07 |
| $ZnCl_2$ | 3.0–5.0 | Protein source | |
| Stock B | | Egg yolk (dry) | 140.00–200.0 |
| $K_2HPO_4$ | 44.25–74.0 | | |
| $Na_2HPO_4.7H_2O$ | 6.0–10.0 | | |
| Stock C | | | |
| $MnSO_4.H_2O$ | 0.6–1.0 | | |
| $MgSO_4.7H_2O$ | 72.0–120.0 | | |
| $CuSO_4$ | 3.0–5.0 | | |

TABLE 2

Amount (mg/100 ml diet) of amino acids in four artificial diets for in vitro rearing of *Catolaccus grandis*.

| Amino Acid | α-1 | α-2 | β & γ |
|---|---|---|---|
| Alanine | 186 | 195 | 290 |
| Arginine | 106 | 111 | 180 |
| Asparagine | 240 | 252 | 360 |
| Aspartic Acid | 7 | 8 | 20 |
| Cysteine | 286 | 300 | 110 |
| Glutamine | 47 | 50 | 310 |
| Glutamic Acid | 560 | 588 | 510 |
| Glycine | 174 | 182 | 180 |
| Histidine | 603 | 633 | 900 |
| Hydroxyproline | 0 | 0 | 0 |
| Isoleucine | 141 | 148 | 110 |
| Leucine | 154 | 162 | 110 |
| Lysine | 218 | 229 | 360 |
| Methionine | 73 | 77 | 110 |
| Phenylalanine | 205 | 216 | 180 |
| Proline | 761 | 800 | 710 |
| Serine | 191 | 201 | 310 |
| Threonine | 424 | 445 | 220 |
| Tryptophan | 366 | 384 | 360 |
| Tyrosine | 992 | 1041 | 360 |
| Valine | 266 | 279 | 310 |
| Total | 6000 | 6300 | 6000 |

TABLE 3

Amounts (mg/100 ml diet) of vitamins in four artificial diets for in vitro rearing of *Catolaccus grandis*.

| Vitamin | α-1 & α-2 | β & γ |
|---|---|---|
| Biotin | 0.06 | 0.048 |
| d-Pantothenic Acid(hemi Ca) | 2.00 | 1.60 |
| Choline Cl | 200.00 | 160.00 |
| Folic Acid | 0.10 | 0.08 |
| myo-Inositol | 15.00 | 12.00 |
| Niacinamide | 5.00 | 4.00 |
| Pyridoxal HCl | 0.30 | 0.24 |
| Riboflavin | 1.00 | 0.80 |
| Thiamine HCl | 0.20 | 0.16 |
| Vitamin $B_{12}$ | 0.02 | 0.016 |
| Total | 223.68 | 178.944 |

TABLE 4

Amounts (mg/100 ml diet) of lipids in four artificial diets for in vitro rearing of *Catolaccus grandis*.

| Lipid | α-1, α-2, β & γ |
|---|---|
| Cholesterol | 50.0 |
| Linoleic Acid | 24.7 |
| Linolenic Acid | 23.5 |
| Oleic Acid | 55.7 |
| Palmitic Acid | 62.0 |
| Palmitoleic Acid | 12.2 |
| Stearic Acid | 12.5 |
| Other Chemicals | |
| Acetone[a] (ml) | 3.0 |
| Lauryl Sulfate[b] | 100.0 |

| | α-1 & α-2 | β | γ |
|---|---|---|---|
| KOH[c] | 673.4 | 757.0 | 588.0 |

[a] As solvent of lipids (evaporated after mixing).
[b] As homogenizer.
[c] To neutralize PH to 7.0.

TABLE 5

Amounts (mg/100 ml diet) of minerals in four artificial diets for in vitro rearing of *Catolaccus grandis*.

| Inorganic Salts | α-1 & α-2 | β & γ |
|---|---|---|
| Stock A | | |
| $CaCl_2$ | 30.0 | 24.0 |
| $COCl_2.6H_2O$ | 5.0 | 4.0 |

TABLE 5-continued

Amounts (mg/100 ml diet) of minerals in four artificial diets for in vitro rearing of *Catolaccus grandis*.

| Inorganic Salts | α-1 & α-2 | β & γ |
|---|---|---|
| FeCl$_3$.6H$_2$O | 20.0 | 16.0 |
| ZnCl$_2$ | 5.0 | 4.0 |
| Stock B | | |
| K$_2$HPO$_4$ dibasic | 74.0 | 59.0 |
| Na$_2$HPO$_4$ dibasic | 10.0 | 8.0 |
| Stock C | | |
| MgSO$_4$.7H$_2$O | 120.0 | 96.0 |
| CuSO$_4$.5H$_2$O | 5.0 | 4.0 |
| MnSO$_4$.H$_2$O | 1.0 | 0.8 |
| Total | 270.0 | 215.8 |

TABLE 6

Amounts (mg/100 ml diet) of other ingredients in four artificial diets for in vitro rearing of *Catolaccus grandis*.

| Compound | α-1, α-2, β, γ |
|---|---|
| Carbohydrate | 250.00 |
| d-glucose | |
| Antibiotic | 1.05 |
| Antimycotic | |
| Fungicide | 1.02 |
| Phosphoric Acid | |
| Antioxidant | 62.07 |
| Propionic Acid | |

| | α-1 | α-2 | β | γ |
|---|---|---|---|---|
| Water | 92175.18 | 91875.18 | 92190.52 | 92359.52 |

| Supplement | α-1, α-2, β | γ |
|---|---|---|
| Egg Yolk | 20%[a] | 13.35 |
| Agar | 0 | 0.755 |

[a] 20 ml fresh egg yolk on 80 ml of diet added after diet preparation.
[b] 13.35 g dry egg yolk on 86.65 g of basic diet to produce supplemented diet
[c] 10.78 g 7% agar solution on 89.22 g of supplemented diet.

TABLE 7

Comparison of weight (mg) of female *Catolaccus grandis* pupae reared in five different artificial diets and in vivo[a]

| Diet | n | x ± S[b] |
|---|---|---|
| Control[c] | 224 | 5.5 ± 0.52a |
| β | 125 | 4.4 ± 0.23b |
| α-2 | 186 | 4.2 ± 0.49b |
| γ | 204 | 4.1 ± 0.34b |
| α-1 | 180 | 4.0 ± 0.19b |
| Guerra et al.[d] | 116 | 2.3 ± 0.32c |

*Insects held at 27 ± 1° C., 60 ± 5% RH, 14:10 L:D.
[b] Means with different letter are significantly different at α 0.05.
[c] Reared in encapsulated third instar boll weevils.
[d] Modified see text.
n = sample size

TABLE 8

Comparison of fecundity of *Catolaccus grandis* females reared in five different artificial diets and in vivo, at 27° C. constant temperature.

| Diet | n | Eggs/Female[a]<br>x ± S[c] | Daily Oviposition[b]<br>x ± S[c] |
|---|---|---|---|
| Control[d] | 49 | 294.2 ± 53.4a | 19.6 ± 3.56a |
| γ | 62 | 217.2 ± 49.1b | 14.5 ± 3.27b |
| α-1 | 47 | 214.3 ± 63.7b | 14.3 ± 4.25b |
| α-2 | 39 | 210.6 ± 65.9b | 14.0 ± 4.39b |
| β | 52 | 208.5 ± 60.0b | 13.9 ± 4.00b |
| Guerra et al.[e] | 49 | 104.4 ± 50.6c | 7.0 ± 3.37c |

[a] For a 15 day period.
[b] Eggs per female/day.
[c] Means with different letter are significantly different at α 0.05.
[d] Reared in encapsulated third instar boll weevils.
[e] Modified see text.
n = sample size.

TABLE 9

Comparison of progeny sex ratio and females produced per female *Catolaccus grandis* reared in five different artificial diets and in vivo, at 27° C. constant temperature.

| Diet | n | Female Pupae per Female[a]<br>x ± S[c] | Progeny Sex Ratio[b]<br>x ± S[c] |
|---|---|---|---|
| Control[d] | 49 | 33.6 ± 19.0a | 4.84 ± 5.88a |
| α-2 | 39 | 27.4 ± 12.8ab | 4.65 ± 3.67ab |
| γ | 62 | 27.4 ± 17.3b | 3.61 ± 3.65ab |
| α-1 | 46 | 25.8 ± 14.5b | 3.58 ± 3.08ab |
| β | 52 | 25.6 ± 14.4b | 3.15 ± 3.54bc |
| Guerra et al.[e] | 45 | 12.2 ± 12.1c | 1.83 ± 2.30c |

[a] For a 15 day period.
[b] In females per male.
[c] Means with different letter are significantly different at α 0.05.
[d] Reared in encapsulated third instar boll weevils.
[e] Modified see text.
n = sample size.

TABLE 10

Life table analysis of *Catolaccus grandis* females reared in five different artificial diets and in vivo, at 27 ± 1° C. and 60 ± 5% RH.

| Alive Females | | $l_x$[a] | $R_e$[b] |
|---|---|---|---|
| Control | 79 | 0.620 | 143.66 |
| α-1 | 97 | 0.485 | 77.92 |
| α-2 | 78 | 0.500 | 85.09 |
| β | 75 | 0.693 | 93.70 |
| γ | 73 | 0.849 | 116.36 |
| Guerra et al.[c] | 79 | 0.620 | 29.85 |

[a] For a 17 days period.
[b] Mean oviposition rate times proportion of females in progeny.
[c] Modified, see text.

TABLE 11

Densities[a] of different live boll weevil immature stages observed an experimental cotton plot in Monte Alto, Texas. Estimated from 15 random samples.

| Date | Eggs | L1 | L2 | L3 | Pupa |
|---|---|---|---|---|---|
| MAY 16 | 0.00 | 0.60 | 0.00 | 0.00 | 0.00 |
| MAY 23 | 1.79 | 1.85 | 0.00 | 0.40 | 0.13 |

TABLE 11-continued

Densities[a] of different live boll weevil immature stages
observed an experimental cotton plot in Monte Alto, Texas.
Estimated from 15 random samples.

| Date | Eggs | L1 | L2 | L3 | Pupa |
|---|---|---|---|---|---|
| MAY 30 | 4.76 | 1.79 | 0.60 | 0.53 | 0.07 |
| JUNE 6 | 4.76 | 4.17 | 0.66 | 1.80 | 0.07 |
| JUNE 13 | 11.31 | 13.16 | 4.63 | 5.32 | 1.87 |

[a]In insects per $m^2$

TABLE 12

Percentage of apparent parasitism by *Catolaccus grandis* of
susceptible immature stages of the boll weevil on the ground.

| Date | Second Instars | Third Instars | Pupa | All Stages |
|---|---|---|---|---|
| MAY 16 | — | — | — | — |
| MAY 23 | 100.00 | 57.14 | 0.00 | 55.56 |
| MAY 30 | 100.00 | 46.67 | 75.00 | 57.14 |
| JUNE 6 | 50.00 | 40.00 | 0.00 | 39.39 |
| JUNE 13 | 36.36 | 18.42 | 20.00 | 20.49 |

Unexplained mortality was excluded from these calculations.

TABLE 13

Percentage of apparent mortality unexplained and induced by
parasitism by *Catolaccus grandis* observed in different boll weevil
immature stages on the ground.

| | Second Instars | | Third Instars | | Pupa | |
|---|---|---|---|---|---|---|
| Date | Un. | P. | Un. | P. | Un. | P. |
| MAY 16 | — | — | — | — | — | — |
| MAY 23 | 33.3 | 66.7 | 6.7 | 53.3 | 0.0 | 0.0 |
| MAY 30 | 60.0 | 40.0 | 6.3 | 43.8 | 0.0 | 75.0 |
| JUNE 6 | 90.5 | 4.8 | 23.1 | 30.8 | 66.7 | 0.0 |
| JUNE 13 | 42.1 | 21.1 | 16.5 | 15.4 | 2.8 | 19.4 |

We claim:

1. In a growth medium for rearing insect ectoparasitoids comprising an amino acid component, a mineral component, a vitamin component, a lipid component, and a carbohydrate component;

wherein the improvement comprises said amino acid component, mineral component, vitamin component, lipid component, and carbohydrate component being present in amounts and proportions effective to support growth of *Catolaccus grandis,* and further wherein said amino acid component comprises by weight, 3.1–4.83% alanine, 1.77–3.0% arginine, 4.0–6.0% asparagine, 1.83–4.77% cysteine, 8.5–9.33% grutamic acid, 0.78–5.17% glutamine, 2.9–3.0% glycine, 10.05–15.0% histidine, 1.83–2.35% isoleucine, 1.83–2.57% leucine, 3.63–6.00% lysine, 1.22–1.67% methionine, 3.0–3.42% phenylalanine, 11.83–12.68% proline, 3.18–5.17% serine, 3.67–7.07% threonine, 6.0–6.1% tryptophan, 6.0–16.53% tyrosine and 4.43–5.17% valine, and further comprises 0–0.33% aspartic acid.

2. The growth medium of claim 1 comprising between about 5800–6500 mg of said amino acid component per 100 ml of said medium.

3. The growth medium of claim 1 further comprising a protein.

4. The growth medium of claim 3 wherein said protein source is from egg yolk.

5. The growth medium of claim 1 wherein said lipid component comprises linoleic acid, linolenic acid, oleic acid, palmitic acid, palmitoleic acid, and stearic acid, in an emulsified form.

6. The growth medium of claim 5 wherein said lipid component further comprises cholesterol.

7. The growth medium of claim 1 wherein said lipid component comprises olive oil and further comprises a surfactant.

8. The growth medium of claim 7 wherein said lipid component further comprises cholesterol.

9. The growth medium of claim 1 wherein said carbohydrate component comprises glucose or trehalose.

10. The growth medium of claim 1 further comprising one or more antimicrobial agents.

11. The growth medium of claim 10 wherein said antimicrobial an antimycotic agent.

12. The growth medium of claim 1 further comprising an antioxidant.

13. The growth medium of claim 1 wherein said mineral component comprises $CaCl_2$, $CoCl_2$, $FeCl_3$, $ZnCl_2$, $K_2HPO_4$, $Na_2HPO_4$, $MnSO_4$, $MgSO_4$ and $CuSO_4$.

14. The growth medium of claim 1 wherein said vitamin component comprises biotin, Ca pantothenate, choline chloride, folic acid, myo-inositol, nicotinamide, pyridoxal HCl, riboflavin, and thiamine.

15. The growth medium of claim 14 wherein said vitamin component further comprises vitamin B12.

16. The growth medium of claim 6 wherein at least a portion of said cholesterol is from egg yolk.

17. The growth medium of claim 8 wherein at least a portion of said cholesterol is from egg yolk.

18. The growth medium of claim 10 wherein said antimicrobial agent is phosphoric acid.

* * * * *